United States Patent
Balavoine et al.

(10) Patent No.: US 9,187,418 B2
(45) Date of Patent: Nov. 17, 2015

(54) METHOD FOR THE PREPARATION OF (3S, 3S') 4,4'-DISULFANEDIYLBIS (3-AMINOBUTANE 1-SULFONIC ACID)

(75) Inventors: Fabrice Balavoine, Paris (FR);
Jonathan Madec, Chatou (FR);
Jean-Marie Schneider, Magnanville (FR); Gérard Coquerel, Boos (FR);
Nicolas Couvrat, Rouen (FR); Yohann Cartigny, Bois Guillaume (FR);
Marie-Noëlle Petit, Mont Saint-Aignan (FR)

(73) Assignee: QUANTUM GENOMICS, Paris (FR)

( * ) Notice: Subject to any disclaimer, the term of this patent is extended or adjusted under 35 U.S.C. 154(b) by 150 days.

(21) Appl. No.: 13/878,003

(22) PCT Filed: Oct. 7, 2011

(86) PCT No.: PCT/EP2011/067524
§ 371 (c)(1),
(2), (4) Date: May 6, 2013

(87) PCT Pub. No.: WO2012/045849
PCT Pub. Date: Apr. 12, 2012

(65) Prior Publication Data
US 2013/0231500 A1    Sep. 5, 2013

(30) Foreign Application Priority Data

Oct. 7, 2010  (EP) .................................... 10306099

(51) Int. Cl.
*C07C 319/24*    (2006.01)
*C07C 303/22*    (2006.01)
*C07C 323/66*    (2006.01)

(52) U.S. Cl.
CPC ............. *C07C 319/24* (2013.01); *C07C 303/22* (2013.01); *C07C 323/66* (2013.01)

(58) Field of Classification Search
None
See application file for complete search history.

(56) References Cited

U.S. PATENT DOCUMENTS

2006/0135602 A1 * 6/2006 Fournie-Zaluski et al. ... 514/517

OTHER PUBLICATIONS

International Search Report for PCT/EP2011/067524, mailed Jan. 24, 2012, Sen, Alina.
Written Opinion of the International Searching Authority for PCT/EP2011/067524, mailed Jan. 24, 2012, Sen, Alina.
Chauvel, E.N. et al., "Investigation of the Active Site of Aminopeptidase A Using a Series of New Thiol-Containing Inhibitors", Journal of Medicinal Chemistry, vol. 37, No. 9, (Jan. 1, 1994), pp. 1339-1346.
Chauvel, E.N. et al., "Differential Inhibition of Aminopeptidase A and Aminopeptidase N by New β-Amino Thiols", Journal of Medicinal Chemistry, vol. 37, No. 18, (Jan. 1, 1994), pp. 2950-2957.
Inguimbert, N. et al., "Synthesis and Separation of Tritiated Inhibitors of Aminopeptidase A and their Prodrugs", Journal of Labelled Compounds and Radiopharmaceuticals, vol. 47, (2004), pp. 997-1005.
Martin, L. et al., "β-Amino-Thiols Inhibit the Zinc Metallopeptidase Activity of Tetanus Toxin Light Chain", Journal of Medicinal Chemistry, vol. 41, No. 18, (Aug. 27, 1998), pp. 3450-3460.

* cited by examiner

*Primary Examiner* — Karl J Puttlitz
(74) *Attorney, Agent, or Firm* — Nixon & Vanderhye P.C.

(57) ABSTRACT

The present invention relates to a new method for the preparation of (3S,3S') 4,4'-disulfanediylbis(3-aminobutane 1-sulfonic acid) in five steps from (S)-ethyl 2-(benzyloxycarbonylamino)-4-(neopentyloxysulfonyl)butanoate A.

18 Claims, 2 Drawing Sheets

METHOD FOR THE PREPARATION OF (3S, 3S') 4,4'-DISULFANEDIYLBIS (3-AMINOBUTANE 1-SULFONIC ACID)

This application is the U.S. national phase of International Application No. PCT/EP2011/067524, filed 7 Oct. 2011, which designated the U.S. and claims priority to EP Application No. 10306099.2, filed 7 Oct. 2010, the entire contents of each of which are hereby incorporated by reference.

The present invention relates to a new method for the preparation of (3S,3S') 4,4'-disulfanediylbis(3-aminobutane 1-sulfonic acid) in five steps from (S)-ethyl 2-(benzyloxycarbonylamino)-4-(neopentyloxysulfonyl)butanoate A. (3 S,3 S') 4,4'-disulfanediylbis(3-aminobutane 1-sulfonic acid) is referred to as "Compound I" in the present invention.

Compound I is a dimer of the selective aminopeptidase A (APA) inhibitor 3-amino 4-mercaptobutanesulfonic acid (also called EC33 in previous documents), generated by creating a disulfide bond between thiol extremities of two 3-amino 4-mercaptobutanesulfonic acid molecules. Dimerisation affords a molecule more amenable to cross the blood-brain barrier as a prodrug. Compound I (also called RB150 in previous documents) has been proven to be an efficient anti-hypertensor agent, as described by Bodineau et al. in *Hypertension* 2008 51, 1318-1325.

Compound I and use thereof as anti-hypertensor were disclosed in the patent application WO2004/007441. The example of process provided in this document to synthesise compound I allows its formation, in 6 steps, from L-Homoserin. Technical specifications, particularly numbers of equivalents, solvents and/or purification techniques involved in this process, do not allow it to be efficiently and easily converted into an industrial scale.

A permanent aim in organic synthesis is to create synthesis processes that can be transposed into industrial conditions. In order to meet requirements for industrial processes, different parameters of the synthesis are to be optimized. First, solvents must be as little volatile as possible, in order to be easily recoverable. Thus, chlorinated volatile solvents, e.g. dichloromethane, chloroform and/or carbon tetrachloride, are preferably avoided. In addition, the numbers of equivalents of reagents required are preferably limited, the temperatures involved preferably remain in an easily accessible range, and easy to proceed purification steps should be privileged. Finally, reaction mixtures and isolated product are preferably thermally stable.

Current Good Manufacturing Practice (c-GMP) has been defined for preparation of drug products for administration to humans or animals. GMP regulations require a quality approach to manufacturing, enabling companies to minimize or eliminate instances of contamination, mixups, and errors. GMP regulations address issues including recordkeeping, personnel qualifications, sanitation, cleanliness, equipment verification, process validation, and complaint handling.

To the Applicant knowledge, no industrially applicable process to synthesise compound I has been described so far.

Hence, an object of the present invention is to provide a process for preparing compound I that can be adapted easily and efficiently to industrial scale, as compared to the process of the prior-art, wherein toxic solvents, such as dimethylformamide, and column chromatography are used.

Moreover, since a highly pure form, typically greater than 99.5 percent, of any drug is generally required for human treatment, a method that combines the control of the formation of isomers and a facile final purification is particularly advantageous.

METHOD

The present invention relates to a new method for the preparation of compound I, more particularly in 5 steps, from (S)-ethyl 2-(benzyloxycarbonylamino) 4-(neopentyloxysulfonyl)butanoate A. Scheme 1 illustrates the successive steps leading from A to compound I.

Unless otherwise stated, the following abbreviations and denominations are used throughout the description and claims of the present invention:
Et=ethyl; tBu=tert-butyl; $CH_2$-tBu=neopentyl=2,2-dimethylpropyl
Cbz=Carbobenzyloxy
Ms=mesyl=$SO_2CH_3$
TFA=trifluoroacetic acid
THF=tetrahydrofuran
MTBE=methyltert-butylether
HPLC=High Performance Liquid Chromatography
ee=enantiomeric excess Each reaction described herein may be performed in solid phase or in liquid phase. Liquid phase reactions may be preferably performed in a solvent selected from organic or aqueous solvents, for example THF, ethanol, chloroform, MTBE, toluene, acetone, TFA, and/or anisole.

Scheme 1:

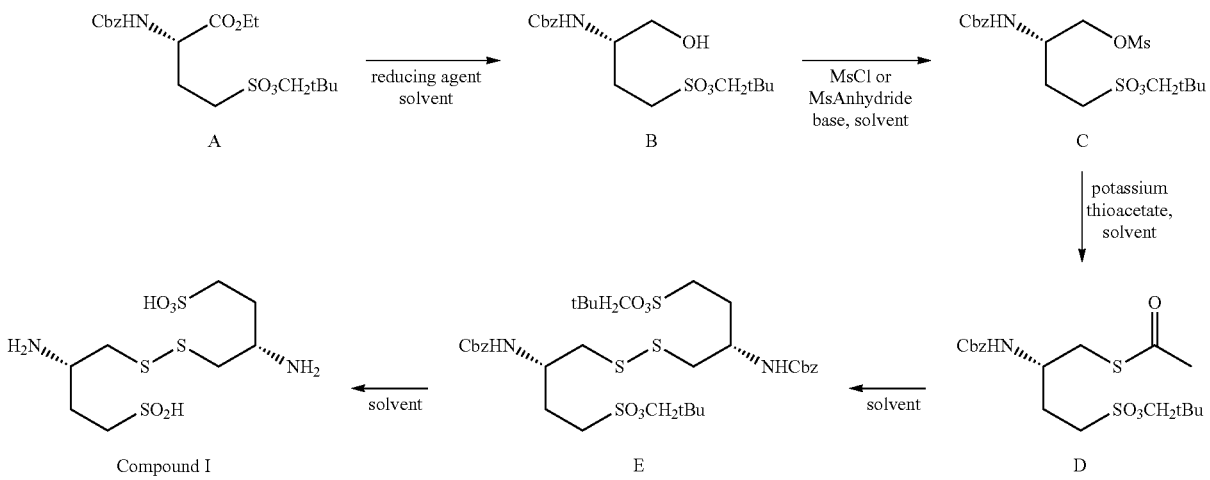

The first object of the present invention relates to a general method for the preparation of compound I from A, comprising the following steps:

(a) reducing the ethyl ester of A, to give (S)-neopentyl 3-(benzyloxycarbonylamino) 4-hydroxybutane 1-sulfonate B;

(b) reacting the alcohol B with methanesulfonic anhydride or methanesulfonyl chloride in presence of a base, to give (S)-neopentyl 3-(benzyloxycarbonylamino) 4-(methylsulfonyloxy)butane 1-sulfonate C;

(c) reacting the mesylated alcohol C with potassium thioacetate, to give (S) 2-(benzyloxycarbonylamino) 4-(neopentyloxysulfonyl)butyl thioacetate D;

(d) dimerizing D to give (3S,3S') neopentyl 4,4'-disulfanediylbis(3-(benzyloxycarbonylamino)butane 1-sulfonate) E; and (e) deprotecting sulfonic ester and amine groups of E, to give (3S,3S') 4,4'-disulfanediylbis(3-aminobutane 1-sulfonic acid) compound I.

The above described method is referred to as "the general method" in the present description.

Preferably, step (a) may be performed by reacting A with a reducing agent-solvent couple selected from $NaBH_4$/LiCl— mixture of THF and ethanol, preferably in 1:1 volume ratio, and $LiBH_4$—THF, more preferably $LiBH_4$—THF. The reaction may be performed at a temperature from about 0° C. to about 25° C., preferably from about 20° C. to about 25° C.

More preferably, step (a) may be performed by reacting A with $LiBH_4$—THF, at a temperature from about 20° C. to about 25° C.

The use of $LiBH_4$, that is soluble and stable in THF, represents an undeniable safety improvement; particularly, it allows use of neat THF as solvent and hence avoids liberation of hydrogen gas due to decomposition of sodium borohydride in ethanol.

Preferably, step (b) may be performed in presence of triethylamine. The reaction may be performed in a solvent selected from chloroform and a mixture of MTBE and toluene, preferably a mixture of MTBE and toluene, preferably in 3:2 volume ratio. The reaction may be performed at a temperature from about –10° C. to about 10° C., preferably from about 5° C. to about 10° C.

Industrial transposition of a synthesis requires volatile solvents to be preferably replaced with less volatile, and/or easier to recover solvents. More preferred conditions for step (b) in this invention include replacement of chloroform with a less volatile and/or easier to recover solvent, such as a mixture of MTBE and toluene in 3:2 volume ratio.

More preferably, step (b) may be performed in presence of triethylamine in a mixture of MTBE and toluene in 3:2 volume ratio, at a temperature from about 5° C. to about 10° C.

Preferably, step (c) may be performed in a solvent selected from ethanol and acetone, preferably acetone. The reaction may be performed at a temperature from about 15° C. to about 25° C.

More preferably, step (c) may be performed in acetone, at a temperature from about 15° C. to about 25° C.

Preferably, step (d) may be performed by first contacting D with sodium hydroxide. The obtained mixture may then be reacted with iodine. The solvent may be ethanol. The reaction may be performed at a temperature from about 15° C. to about 25° C.

Preferably, step (e) may be performed by stirring E in a mixture of TFA and anisole. More preferably, step (e) may be performed by stirring E in a refluxing mixture of TFA and anisole, preferably in 5:1 volume ratio.

A most preferred form of the present invention is the general method described above, wherein:

step (a) is performed by reacting A with $LiBH_4$—THF, at a temperature from about 20° C. to about 25° C.;

step (b) is performed in presence of triethylamine, in a mixture of MTBE and toluene in 3:2 volume ratio, at a temperature from about 5° C. to about 10° C.;

step (c) is performed in acetone, at a temperature from about 15° C. to about 25° C.;

step (d) is performed by first contacting D with sodium hydroxide, in ethanol, at a temperature from about 15° C. to about 25° C. and then reacting the obtained mixture with iodine, in ethanol, at a temperature from about 15° C. to about 25° C.; and step (e) is performed by stirring E in a refluxing mixture of TFA and anisole in 5:1 volume ratio.

This method comprises (a) to (e) optimised steps for industrial application, in particular steps (b) to (e) are even compliant to c-GMP requirements.

Industrial transposition of a synthesis requires parameters to be optimised. In particular, high enthalpy reactions are preferably avoided. High purity levels are preferred for products. Isolated products are preferably thermally stable.

Table 1 provides the reaction enthalpies, the purities (determined by HPLC and expressed as molar percentages) and the stabilities of the products of each step for this preferred method.

TABLE 1

| | Purity | Enthalpies | Stability |
|---|---|---|---|
| step (a) | 94.0% | $\Delta rH_{(addition\ onto\ LiBH_4)}$ = –235 kJ/mol | Melting at 53° C. |
| | ee 98% | $\Delta rH_{(HCl\ hydrolysis)}$ = –145 kJ/mol | |
| step (b) | 98% | $\Delta rH$ = –253 kJ/mol | Melting at 66° C. Decomposition at 103° C. |
| step (c) | 98% | $\Delta rH$ = –145 kJ/mol | Melting at 72° C. Decomposition at 154° C. |
| step (d) | 97% | $\Delta rH_{(addition\ of\ NaOH)}$ = –49 kJ/mol | Melting at 100° C. |
| | | $\Delta rH_{(addition\ of\ I_2)}$ = –136 kJ/mol | Decomposition at 140° C. |
| step (e) | >99.9% | $\Delta rH$ = –389 kJ/mol | Melting at 78° C. No decomposition observed |

Industrial transposition of a synthesis requires easy purification steps to be preferred, especially the last purification step of the synthesis.

A preferred form of this invention relates to the process of synthesis of compound I as described previously, wherein purification of compound I is performed by recrystallisation in water.

Industrial transposition of a synthesis requires most stable forms of compounds to be preferred, especially the most stable form of the final product.

Studies performed on compound I showed that hydrate forms, particularly trihydrate form, are more stable than neat form of the compound. The trihydrate form compound I, ($3H_2O$) is the most stable form under ambient conditions. Any mixture of hydrates of compound I will evolve within a few days towards the trihydrate form in ambient conditions. Ambient conditions as used herein refer to a temperature between 15° C. and 25° C., at atmospheric pressure, and a relative humidity rate above 50%.

A preferred form of this invention relates to the process of synthesis of compound I as described previously, wherein compound I is obtained as a hydrate form, preferably as the trihydrate form.

Another object of the present invention is thus the crystalline trihydrate form of compound I. In particular, the crystallographic structure of compound I trihydrate is detailed in example 2.

Synthesis of the starting material of the general method described above, (S) ethyl 2-(benzyloxycarbonylamino) 4-(neopentyloxysulfonyl)butanoate A, has been already described in patent application WO2004/007441, as an intermediate in the synthesis of 4,4'-thiobis(3-aminobutane 1-neopentylsulfonate)bis-trifluoroacetate. Isolation thereof can be readily performed by one of ordinary skill in the art if necessary.

Another object of the invention is the general method described above, wherein synthesis of compound A from L-Homocystine comprises the following steps:
(a-1) reacting L-Homocystine with benzyl chloroformate to give (2S,2S') 4,4'-disulfanediylbis(2-(benzyloxycarbonylamino)butanoic acid) F;
(b-1) carrying out an esterification reaction between F and ethanol to give (2S,2S') diethyl 4,4'-disulfanediylbis(2-(benzyloxycarbonylamino)butanoate) G;
(c-1) oxidatively cleaving the disulfide bond of G to give (S) ethyl 2-(benzyloxycarbonylamino) 4-(chlorosulfonyl)butanoate H; and
(d-1) reacting the sulfonyl chloride H with neopentyl alcohol to give (S) ethyl 2-(benzyloxycarbonylamino) 4-(neopentyloxysulfonyl)butanoate A.

The synthesis of A from L-Homocystine is illustrated on Scheme 2.

With the same preoccupations as the ones evoked for the synthesis of compound I from A, the process to synthesize A may be optimized in order to make it as much as possible in accordance with industrial requirements.

Preferably, step (a-1) may be performed in presence of sodium hydroxide. The solvent may be THF. The reaction may be performed at a temperature from about 5° C. to about 25° C., preferably the temperature may remain between about 5° C. and about 10° C. during addition of reagents.

Ease of analysis is an important criterion for a synthesis to be suitable for industry. Presence of Cbz amine protective groups on compound F may make it more appropriate for analysis, particularly for HPLC analysis.

Preferably, step (b-1) may be performed by reacting F with thionyl chloride. The solvent may be pure ethanol. The reaction may be performed at a temperature from about 45° C. to about 55° C.

Preferably, step (c-1) may be performed by reacting G with chlorine. The solvent may be ethanol. The reaction may be performed at a temperature from about 5° C. to about 10° C.

Preferably, step (d-1) may be performed in presence of triethylamine. The solvent may be toluene. The reaction may be performed at a temperature from about 15° C. to about 25° C.

Figure 1:
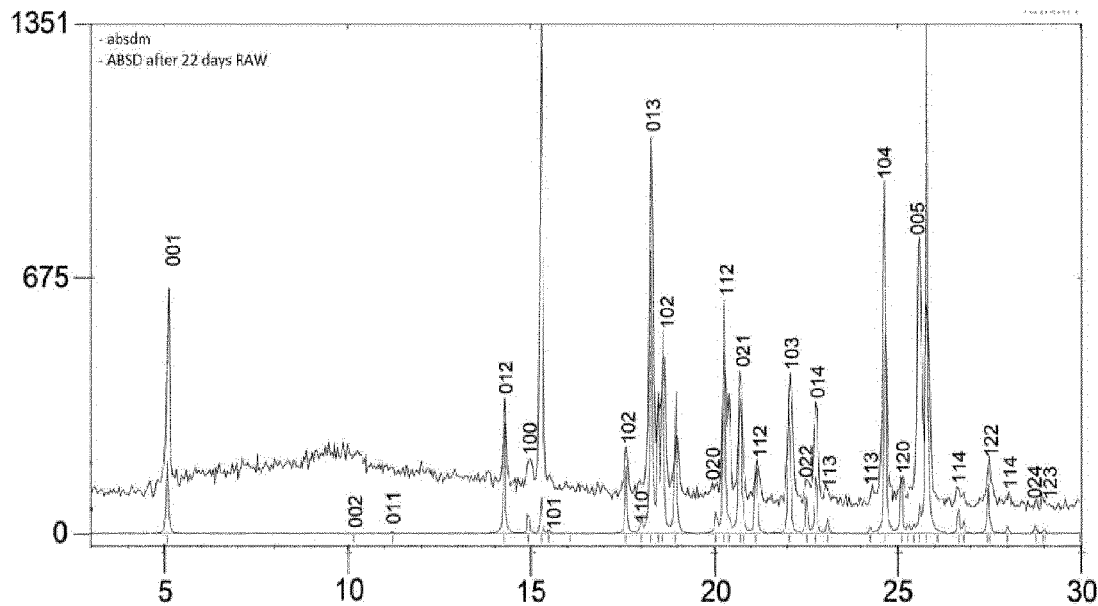
FIG. 1: Compared XRPD (X Ray Powder Diffraction) patterns of compound I trihydrate: calculated from single crystal structure (lower spectrum) and experimental (upper spectrum).

Scheme 2:

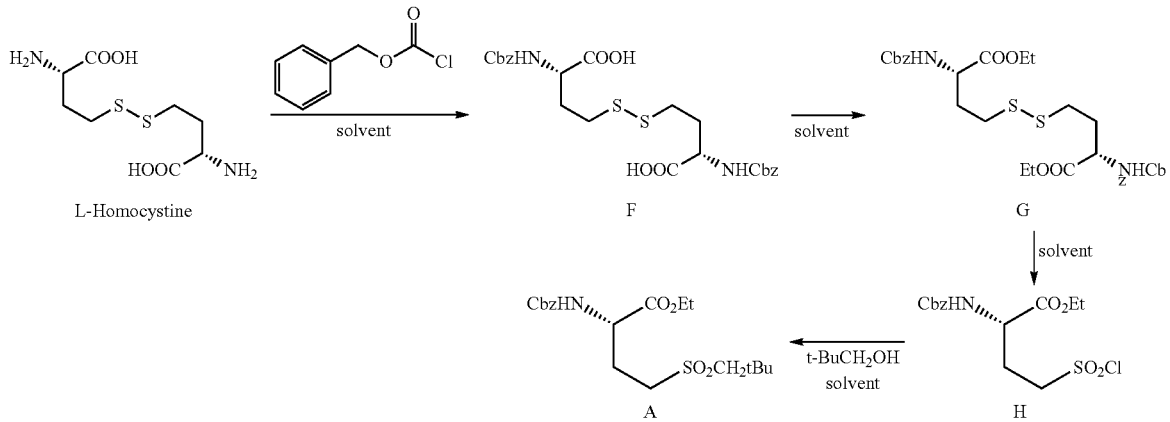

EXAMPLES

Example 1

Synthesis of Compound I from (S) ethyl 2-(benzyloxycarbonylamino) 4-(neopentyloxysulfonyl)butanoate A Step (a): (S) neopentyl 3-benzyloxycarbonylamino) 4-hydroxybutane 1-sulfonate B

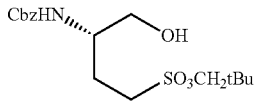

B (S) ethyl 2-(benzyloxycarbonylamino) 4-(neopentyloxysulfonyl)butanoate A (41.55 g, 100.0 mmol, 1.0 eq.) is added dropwise onto a 2M solution of $LiBH_4$ in THF (50 mL, 44.8 g, 100.0 mmol, 1.0 eq.). The addition is performed at room temperature over a 3 hrs period. At the end of the addition, the mixture is stirred at room temperature until conversion is complete (A<1%). Addition of toluene, followed by hydrolysis with HCl, washings of the organic layer with $NaHCO_3$ and water, and concentration under vacuum lead to the desired product as a pale yellow oil in quantitative yield (ee=98%), which slowly crystallises at room temperature in 4 or 5 days.

As B was found to have a very low melting point by DSC analysis, it was not possible to isolate it as a solid by simple crystallisation. It was decided to let it in solution and use it without further purification in the following step.

Step (b): (S) neopentyl 3-(benzyloxycarbonylamino) 4-(methylsulfonyloxy)butane 1-sulfonate C

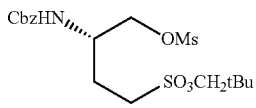

C

A solution of B (57.64 g, 154.34 mmol, 1.0 eq.) in toluene (115 mL, 2.0 vol.) is diluted with MTBE (173 mL, 3.0 vol.) at room temperature. Mesyl chloride (17.9 mL, 26.5 g, 231.50 mmol, 1.5 eq.) is then added at room temperature and the homogeneous mixture is cooled to 10° C. The addition of triethylamine (43.0 mL, 31.2 g, 308.67 mmol, 2.0 eq.) is performed at T<20° C. At the end of the addition, the mixture is stirred at 10° C. until conversion is complete (B<1%). After hydrolysis with diluted HCl, the organic layer is washed with $NaHCO_3$, water and brine, followed by a partial concentration under reduced pressure. The corresponding mesylate is then crystallised by addition of heptanes (5.0 vol.) at 40° C. After cooling, filtration and drying, the expected product is isolated as a whitish solid in 92.5% yield and with a very high chemical purity (98%).

Step (c): (S) 2-(benzyloxycarbonylamino) 4-(neopentyloxysulfonyl)butyl thioacetate D

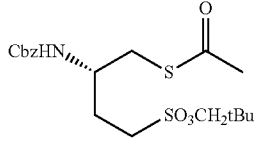

D

A solution of mesylate C (81.3 g, 180.05 mmol, 1.0 eq.) in acetone (203 mL, 2.5 vol.) is added dropwise to a suspension of potassium thioacetate (41.1 g, 360.1 mmol, 2.0 eq.) in acetone (203 mL, 2.5 vol.) at room temperature and over a period of 2 hrs. The reaction mixture is stirred at room temperature until conversion is complete (C<1%). After filtration of the salts and addition of toluene (4.0 vol.), acetone is removed by distillation under reduced pressure at 25° C. The solution is then treated with active charcoal and concentrated to 2.0 volumes. Slow addition of heptane (5.0 vol.) at room temperature, followed by cooling at 0° C., filtration and drying at 45° C., provides the expected product as a whitish solid in 78.2% yield and with a very high chemical purity (98%).

Step (d): (3S,3S') neopentyl 4,4'-disulfanediylbis(3-(benzyloxycarbonylamino)butane 1-sulfonate) E

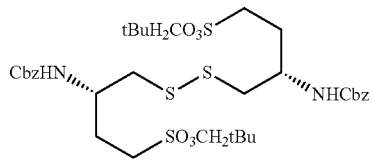

E

A solution of D (59.16 g, 137.1 mmol, 1.0 eq.) suspended in ethanol (203 mL, 2.5 vol.) is cooled to 0° C. 20% sodium hydroxide (25.1 mL, 150.8 mmol, 1.1 eq.) diluted with water (16.9 mL, 0.285 vol.) is then added dropwise to the suspension by keeping the temperature below 10° C. The reaction mixture is warmed to room temperature and stirred until conversion is complete (D<1%). The intermediate thiol reacts at room temperature with a solution of iodine (20.9 g, 82.3 mmol, 0.6 eq.) in ethanol (118 mL, 2.0 vol.). The reaction is complete at the end of the addition of the oxidizing agent. After addition of a $Na_2S_2O_5$ (13.0 g, 68.5 mmol, 0.5 eq.) aqueous solution (118 mL, 2.0 vol.) to reduce the excess of residual iodine, ethanol is removed by distillation under reduced pressure at 40° C. Addition of water (3.0 vol.) at room temperature, followed by cooling at 0° C., filtration and drying at 45-50° C., provides the expected dimer as a white solid in 98.3% yield and with a very high chemical purity (97.0%). The amount of iodide ions, coming from the reduction of iodine, is checked in the sample by potentiometric assay.

$E°(Ag^+/Ag(s))=0.80V$
$Ks_{AgI}=1.5.10^{-16}$
$[AgNO_3]=0.1N$
Electrode: $E=E°(Ag^+/Ag(s))+0.06 \log [Ag^+]$
$[Ag^+]=K_{SI}/[I^-]$
$E=E° (Ag^+/Ag(s))+0.06 \log (K_{SI}/[I^-])$
Assay: $[I^-]$ decreases and E increases
LOD=1 mg Four further washings with water are performed until no more iodide ions are detected. The results are presented in table 2.

TABLE 2

| Washings | 1 | 2 | 3 | 4 |
|---|---|---|---|---|
| I⁻assay (%) | 4.5 | 1.26 | 0.12 | 0.02 |

Step (e): (3S,3S') 4,4'-disulfanediylbis(3-aminobutane 1-sulfonic acid) compound I

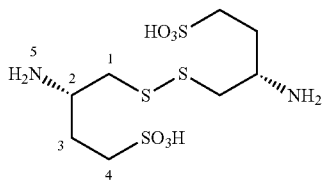

Compound I

A solution of E (44.0 g, 56.6 mmol, 1.0 eq.) in TFA (220 mL, 5.0 vol.) and anisole (44 mL, 1.0 vol.) is heated to reflux (75° C.) and the reaction mixture is stirred in these conditions until conversion is complete (E<1%). TFA is removed by distillation under reduced pressure at 50° C. Slow addition of MTBE (5.0 vol.) at room temperature makes the expected product precipitate. After trituration, filtration and washing with MTBE (1.0 vol.), the crude solid is suspended in methanol (220 mL, 5.0 vol.). New trituration, filtration and washing with MTBE (1.0 vol.), followed by drying under reduced pressure, provides compound I as a white solid in 92.5% yield.

NMR: $^1$H (solvent D$_2$O, 400 MHz, ppm): 4.70 (s, 6H, H$_5$); 3.77 (m, 2H, H$_2$); 3.14 (dd, 2H, H$_1$); 2.98 (dd, 4H, H$_4$); 2.86 (dd, 2H, H$_1$); 2.13 (m, 4H, H$_3$). $^{13}$C (solvent D$_2$O, 100 MHz, ppm): 49.4 (2C, C$_2$); 46.6 (2C, C$_4$); 38.3 (2C, C$_1$); 26.9 (2C, C$_3$).

Example 2

Crystallographic Data of Compound I Trihydrate

Compound I obtained in example 1 was stored for 22 days in ambient conditions in order to exclusively contain trihydrate form.

Data Collection:

The crystal structure of compound I trihydrate [C$_8$S$_4$N$_2$O$_6$H$_{20}$, 3(H$_2$O)], has been determined from single crystal X-Ray diffraction (XRD). The chosen crystal was stuck on a glass fibre and mounted on the full three-circle goniometer of a Bruker SMART APEX diffractometer with a CCD area detector. Three sets of exposures (a total of 1800 frames) were recorded, corresponding to three ω scans (steps of 0.3°), for three different values of φ.

FIG. 1 shows experimental and calculated XRD patterns of compound I trihydrate.

Table 3 presents a selection of calculated reflections from PowderCell for the compound I trihydrate structure and the corresponding experimental peaks positions and intensities. Intensity values of experimental peaks must not be conferred too much importance since preferential orientation effects relying on the crystallization process are very important.

TABLE 3

| h | k | l | 2θ (°) Calculated | d (Å) Calculated | I (%) Calculated | 2θ (°) Experimental | d (Å) Experimental | I (%) Experimental |
|---|---|---|---|---|---|---|---|---|
| 0 | 0 | 1 | 5.08 | 17.39 | 14 | 5.09 | 17.34 | 76 |
| 0 | 1 | 2 | 14.27 | 6.20 | 23 | 14.30 | 6.19 | 23 |
| 0 | 0 | 3 | 15.28 | 5.79 | 7 | 15.30 | 5.79 | 100 |
| −1 | 0 | 2 | 17.60 | 5.03 | 13 | 17.62 | 5.03 | 15 |
| 0 | 1 | 3 | 18.28 | 4.85 | 55 | 18.32 | 4.84 | 96 |
| 1 | 0 | 2 | 18.59 | 4.77 | 40 | 18.61 | 4.76 | 30 |
| 1 | 1 | 1 | 18.95 | 4.68 | 28 | 18.98 | 4.67 | 16 |
| −1 | 1 | 2 | 20.27 | 4.38 | 47 | 20.34 | 4.36 | 26 |
| 0 | 2 | 1 | 20.70 | 4.29 | 37 | 20.75 | 4.28 | 26 |
| 1 | 1 | 2 | 21.15 | 4.20 | 14 | 21.16 | 4.19 | 11 |
| 1 | 0 | 3 | 22.05 | 4.03 | 27 | 22.09 | 4.02 | 37 |
| 0 | 1 | 4 | 22.77 | 3.90 | 12 | 22.79 | 3.90 | 37 |
| −1 | 1 | 3 | 23.11 | 3.85 | 3 | 23.12 | 3.84 | 6 |
| −1 | 0 | 4 | 24.66 | 3.61 | 47 | 24.65 | 3.61 | 74 |
| 1 | 2 | 0 | 25.10 | 3.54 | 13 | 25.15 | 3.54 | 7 |
| 0 | 0 | 5 | 25.60 | 3.48 | 4 | 25.60 | 3.48 | 62 |
| 1 | 2 | 1 | 25.80 | 3.45 | 100 | 25.83 | 3.45 | 39 |
| −1 | 1 | 4 | 26.67 | 3.34 | 5 | 26.66 | 3.34 | 7 |
| 0 | 1 | 5 | 27.54 | 3.24 | 2 | 27.52 | 3.24 | 13 |
| 1 | 1 | 4 | 28.01 | 3.18 | 1 | 28.05 | 3.18 | 4 |
| −1 | 0 | 5 | 28.98 | 3.08 | 1 | 28.94 | 3.08 | 4 |

The cell parameters and the orientation matrix of the crystal were preliminary determined by using SMART Software. Data integration and global cell refinement were performed with SAINT Software. Intensities were corrected for Lorentz, polarisation, decay and absorption effects (SAINT and SADABS Softwares) and reduced to $F_o^2$. The program package WinGX3 was used for space group determination, structure solution and refinement.

Data Refinement:

The standard space group P2$_1$ (n°4) was determined from systematic extinctions and relative $F_o^2$ of equivalent reflections. The structure was solved by direct methods (SIR 92). Anisotropic displacement parameters were refined for all non-hydrogen atoms. Hydrogen atoms were located from subsequent difference Fourier syntheses and placed with geometrical constraints (SHELXL). The final cycle of full-matrix least-square refinement on F2 was based on 3714 observed reflections and 234 variable parameters and converged with unweighted and weighted agreement factors of:

R1=0.0347, wR2=0.0845 for [F$^2$>2σ(F$^2$)] and R1=0.0371, wR2=0.0934 for all data.

The crystals were obtained by slow evaporation of a saturated solution of compound I in water at ambient temperature.

Crystallographic Data:

TABLE 4

| Chemical Formula | C$_8$S$_4$N$_2$O$_6$H$_{20}$, 3(H$_2$O) |
|---|---|
| Molecular Weight/g · mol$^{-1}$ | 422,55 |
| Crystal System | Monoclinic |
| Space Group | P2$_1$ (n°4) |
| Z | 2 |
| Z' (asymmetric units per unit cell) | 1 |
| a/Å | 5.936 (2) |
| b/Å | 8.849 (3) |
| c/Å | 17.416 (7) |
| β (°) | 93.349 (6) |
| V/Å$^3$ | 913.4 (6) |
| dcalc/g · cm$^{-3}$ | 1.536 |
| Temperature/K | 293 (2) |
| Absolute structure parameter | 0.0 (5) |
| Crystal colour | colourless |
| Approximate crystal size/mm | 0.5 × 0.3 × 0.05 |
| F(000)/e− | 448 |
| Absorption coefficient μ (MoKα1)/mm$^{-1}$ | 0.562 |

Table 5 presents the atomic coordinates ($\times 10^4$) and equivalent isotropic displacement parameters ($Å^2 \times 10^3$). U(eq) is defined as one third of the trace of the orthogonalized Uij tensor.

TABLE 5

|  | x | y | z | U(eq) |
|---|---|---|---|---|
| S(1) | −6907 (8) | 11820 (6) | 2086 (3) | 36 (1) |
| S(2) | −120 (8) | 6540 (6) | 3958 (3) | 29 (1) |
| S(1A) | −5005 (10) | 13527 (7) | 2563 (3) | 36 (1) |
| S(2A) | 1135 (8) | 14087 (6) | −658 (3) | 28 (1) |
| O(1) | 1610 (20) | 7004 (18) | 3451 (9) | 39 (4) |
| O(2) | −1390 (30) | 5256 (19) | 3657 (11) | 46 (4) |
| O(3) | 800 (30) | 6300 (20) | 4737 (9) | 52 (5) |
| O(1A) | 2310 (30) | 12720 (20) | −396 (12) | 53 (5) |
| O(2A) | 2380 (30) | 15414 (19) | −407 (9) | 39 (4) |
| O(3A) | 510 (30) | 14090 (30) | −1476 (9) | 53 (5) |
| N(1) | −6330 (30) | 9880 (20) | 3645 (10) | 31 (4) |
| N(1A) | −4670 (30) | 15277 (19) | 942 (9) | 28 (4) |
| C(1) | −5210 (40) | 10160 (30) | 2306 (12) | 35 (5) |
| C(2) | −4410 (40) | 9920 (30) | 3132 (11) | 28 (4) |
| C(3) | −3070 (40) | 8440 (30) | 3193 (12) | 35 (5) |
| C(4) | −2020 (40) | 8090 (20) | 3988 (12) | 31 (4) |
| C(1A) | −2670 (40) | 13690 (30) | 1940 (12) | 35 (5) |
| C(2A) | −3260 (40) | 13880 (30) | 1091 (11) | 27 (4) |
| C(3A) | −1110 (30) | 13990 (30) | 661 (11) | 29 (4) |
| C(4A) | −1460 (40) | 14090 (30) | −199 (11) | 31 (4) |
| OWA | 2000 (30) | 6520 (20) | 1873 (11) | 51 (5) |
| OWB | −9670 (40) | 12120 (20) | 3802 (12) | 56 (5) |
| OWC | −5190 (40) | 9820 (30) | 5188 (12) | 70 (7) |

Figure 2:
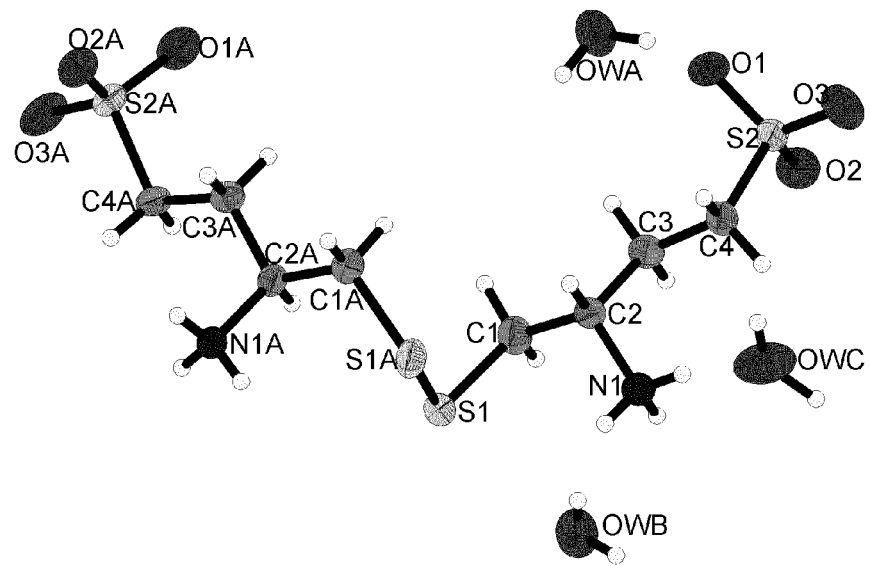
FIG. 2: ORTEP (Oak Ridge Thermal Ellipsoid Plot) representation of compound I trihydrate.

Structural Description:

The asymmetric unit is composed of a single compound I molecule associated with 3 molecules of water. FIG. 2 presents the asymmetric unit of the molecule of compound I and the 3 molecules of water.

Figure 3:
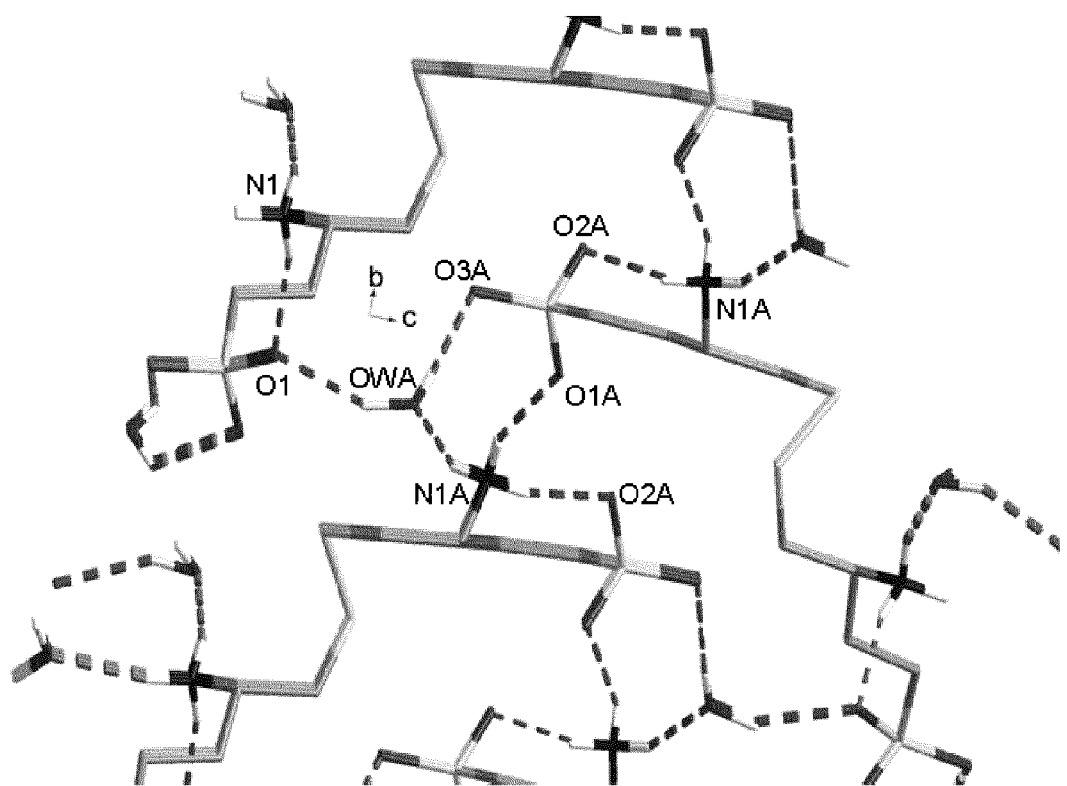
FIG. 3: Projection along an axis of compound I trihydrate. H-bonds are represented by dotted lines.

Along b axis, successive molecules of compound I interact via two kinds of hydrogen bonds established between the oxygen atom O1A and the hydrogen atom H(N1A) (d~1.94 Å), and between the oxygen atom O1 and the hydrogen atom H(N1) (d~1.99 Å). Along a axis, two consecutive molecules of compound I interact via a hydrogen bond between the oxygen atom O2A and the hydrogen atom H(N1A) (d~1.98 Å). These interactions oriented in a and b directions lead to layers parallel to (110). Furthermore, a water molecule (OWA) is inserted between these molecules and establishes three different hydrogen bonds: the first one links the oxygen atom OWA to the hydrogen atom H(N1A) (d~2.02 Å), the second one links the oxygen atom O3A to the hydrogen atom H(OWA) (d~1.94 Å) and the last one links the oxygen atom O1 to H(OWA) (d~1.97 Å). The slices (110) present a thickness of $d_{001}$ (~17.5 Å). The different interactions inside these slices along a axis are represented more specifically on FIG. 3. Two consecutive layers interact along c axis through hydrogen bonds established with the two others water molecules OWB and OWC located in (002) planes. The oxygen atom of the OWB water molecule establishes hydrogen bonds with the hydrogen atom H (from N1) (d~2.00 Å), from a first slice, and is connected to the following slice via a hydrogen bond with the oxygen atom O3 and the hydrogen atom H (from OWB) (d~1.92 Å). The oxygen atom of the OWC water molecule establishes a hydrogen bond with the hydrogen atom H (from N1) (d~1.86 Å) for a first slice, and then is linked to the adjacent slice by the way of two hydrogen bonds through interactions of two oxygen atoms from the sulfonate moiety S2. The oxygen atom O2 and the oxygen atom O3 interact with the two hydrogen atoms of the water molecule OWC with bond lengths of respectively d~2.30 Å and d~2.03 Å.

Example 3

Synthesis of (S) ethyl 2-(benzyloxycarbonylamino)-4-(neopentyloxysulfonyl)butanoate A from L-homocystine Step (a-1): (2S,2S') 4,4'-disulfanediylbis(2-(benzyloxycarbonylamino)butanoic acid) F

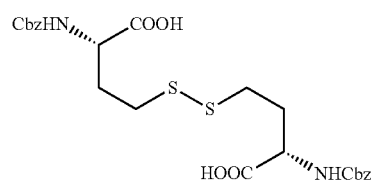

L-Homocystine (200.0 g, 745.5 mmol, 1.0 eq.) is suspended in THF (1000 mL, 5.0 vol.) and cooled to 5-10° C. Addition of 20% sodium hydroxide (521.7 mL, 626.2 g, 125.25 g at 100%, 3.13 mmol, 4.2 eq.) is followed by addition of benzyl chloroformate (220.3 mL, 267 g, 1565.5 mmol, 2.1 eq.). Conversion is complete after a night at room temperature (L-Homocystine<1%). Extractions and washings of the organic layer with water leads to a yellow oil which is isolated in quantitative yield, and which slowly crystallizes as a yellowish solid at room temperature.

Step (b-1): (2S,2S') diethyl 4,4'-disulfanediylbis(2-benzyloxycarbonylamino)butanoate) G

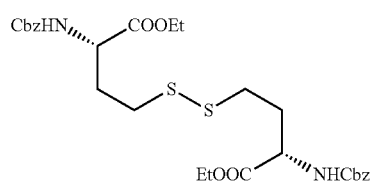

F (140.0 g, 260.89 mmol, 1.0 eq.) is suspended in pure ethanol (700 mL, 5.0 vol.) and heated to 50° C. The addition of SOCl$_2$ (41.6 mL, 68.3 g, 573.96 mmol, 2.2 eq.) is run at 50° C. to avoid accumulation. Conversion is complete (F<1%) after 1 hr at 50° C. Concentration of the crude mixture followed by dissolution in ethyl acetate and washings of the organic layer leads to a clear solution which is partially concentrated. Slow addition of 5.0 volumes of heptane leads to crystallisation of the desired product as a white solid. After filtration and drying, the bis-ester is isolated in 92% yield.

Step (c-1): (S) ethyl 2-benzyloxycarbonylamino-4-(chlorosulfonyl)butanoate H

G (100.0 g, 168.7 mmol, 1.0 eq.) is suspended in ethanol (500 mL, 5.0 vol.) and cooled to 5° C. The addition of Cl$_2$ (83.7 g, 1.18 mol, 7.5 eq.) is performed at T<10° C. Conversion is complete (G<1%) when the reaction mixture is perfectly homogeneous. The sulfonyl chloride solution is poured onto a mixture of an aqueous carbonate solution and toluene, keeping the temperature below 20° C. Washings of the organic layer, followed by concentration under reduced pressure, lead to the desired product as a colorless oil in 96.8% yield.

The expected product can be isolated as a white solid when 5.0 volumes of heptane are slowly added to a concentrated toluene solution (2.0 vol.) of the product. Nevertheless, the purity is not really improved and the yield dramatically decreases (75-80%). Consequently, the sulfonyl chloride H is isolated in 1.0 volume of toluene and used without further purification in the following step.

Step (d-1): (S) ethyl 2-(benzyloxycarbonylamino) 4-neopentyloxysulfonyl)butanoate A

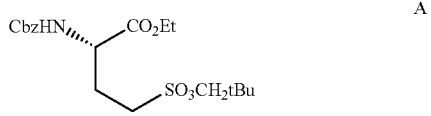

Neopentyl alcohol (29.1 g, 329.84 mmol, 1.2 eq.) is dissolved in toluene (400 mL, 4.0 vol.) and a solution of H (100.0 g, 274.87 mmol, 1.0 eq.) in toluene (100 mL, 1.0 vol.) is added at room temperature. The homogeneous mixture is then cooled to 0° C. The addition of triethylamine (46.0 mL, 33.4 g, 329.84 mmol, 1.2 eq.) is performed at 0° C. At the end of the addition, the mixture is warmed to room temperature until conversion is complete (H<1%). After hydrolysis with dilute HCl, the organic layer is washed with NaHCO$_3$, water and brine, and concentrated under reduced pressure to give the desired product as a pale yellow oil in 94.4% yield.

The invention claimed is:

1. A process for preparing (3S,3S') 4,4'-disulfanediylbis(3-aminobutane 1-sulfonic acid) from (S) ethyl 2-(benzyloxycarbonylamino) 4-(neopentyloxysulfonyl)butanoate A comprising the steps of:
   (a) reducing the ethyl ester of A to give (S) neopentyl 3-(benzyloxycarbonylamino) 4-hydroxybutane 1-sulfonate B;
   (b) reacting the alcohol B with methanesulfonic anhydride or methanesulfonyl chloride in presence of a base to give (S) neopentyl 3-(benzyloxycarbonylamino) 4-(methylsulfonyloxy)butane 1-sulfonate C;
   (c) reacting the mesylated alcohol C with potassium thioacetate to give (S) 2-(benzyloxycarbonylamino) 4-(neopentyloxysulfonyl)butyl thioacetate D;
   (d) dimerizing D to give (3S,3S') neopentyl 4,4'-disulfanediylbis(3-(benzyloxycarbonylamino)butane 1-sulfonate) E; and
   (e) deprotecting sulfonic ester and amine groups of E to give (3S,3S') 4,4'-disulfanediylbis(3-aminobutane 1-sulfonic acid).

2. The process according to claim 1, wherein step (a) is performed by reacting A with a reducing agent—solvent couple selected from NaBH$_4$/LiCl—mixture of THF and ethanol and LiBH$_4$—THF, at a temperature from about 0° C. to about 25° C.

3. The process according to claim 1, wherein step (a) is performed by reacting A with LiBH$_4$—THF, at a temperature from about 20° C. to about 25° C.

4. The process according to claim 1, wherein step (b) is performed in presence of triethylamine as base, in a solvent selected from chloroform and a mixture of MTBE and toluene, at a temperature from about −10° C. to about 10° C.

5. The process according to claim 1, wherein step (b) is performed by reacting B with methanesulfonyl chloride, in presence of triethylamine as base, in a mixture of MTBE and toluene in 3:2 volume ratio, at a temperature from about 5° C. to about 10° C.

6. The process according to claim 1, wherein step (c) is performed in a solvent selected from ethanol and acetone.

7. The process according to claim 1, wherein step (c) is performed in acetone, at a temperature from about 15° C. to about 25° C.

8. The process according to claim 1, wherein step (d) is performed by contacting D with sodium hydroxide, in ethanol, and reacting the obtained mixture with iodine, in ethanol, at a temperature from about 15° C. to about 25° C.

9. The process according to claim 1, wherein step (e) is performed by stirring E in a mixture of TFA and anisole.

10. The process according to claim 1, wherein step (e) is performed by stirring E in a refluxing mixture of TFA and anisole, in 5:1 volume ratio.

11. The process according to claim 1, wherein purification of the final product is performed by recrystallisation in water.

12. The process according to claim 1, wherein the final product is obtained as one of its hydrate forms.

13. The process according to claim 1, wherein A is prepared from L-Homocystine by a process comprising the steps of:
   (a-1) reacting L-Homocystine with benzyl chloroformate to give (2S,2S') 4,4'-disulfanediylbis(2-(benzyloxycarbonylamino)butanoic acid) F;
   (b-1) carrying out an esterification reaction between F and ethanol to give (2S,2S') diethyl 4,4'-disulfanediylbis(2-(benzyloxycarbonylamino)butanoate) G;
   (c-1) oxidatively cleaving the disulfide bond of G to give (S) ethyl 2-(benzyloxycarbonylamino) 4-(chlorosulfonyl)butanoate H and
   (d-1) reacting H with neopentyl alcohol to give (S) ethyl 2-(benzyloxycarbonylamino) 4-(neopentyloxysulfonyl) butanoate A.

14. The process according to claim 13, wherein step (a-1) is performed in THF in presence of sodium hydroxide, at a temperature from about 15° C. to about 25° C.

15. The process according to claim 13, wherein step (b-1) is performed by reacting F with thionyl chloride, in pure ethanol, at a temperature from about 45° C. to about 55° C.

16. The process according to claim 13, wherein step (c-1) is performed by reacting G with chlorine, in ethanol, at a temperature from about 5 to about 10° C.

17. The process according to claim 13, wherein step (d-1) is performed in presence of triethylamine, in toluene, at a temperature from about 15° C. to about 25° C.

18. The process according to claim 1, wherein the final product is obtained as its trihydrate form.

* * * * *